United States Patent
Albert et al.

(10) Patent No.: US 9,199,919 B2
(45) Date of Patent: Dec. 1, 2015

(54) PROCESS FOR THE PREPARATION OF CHIRAL HYDRAZIDES

(75) Inventors: Martin Albert, Kundl/Tyrol (AT);
Dominic De Souza, Holzkirchen (DE);
Joerg Salchenegger, Kundl/Tyrol (AT);
Michael Oberhuber, Bozen (IT)

(73) Assignee: SANDOZ AG, Basel (CH)

(*) Notice: Subject to any disclaimer, the term of this patent is extended or adjusted under 35 U.S.C. 154(b) by 387 days.

(21) Appl. No.: 13/697,800

(22) PCT Filed: May 18, 2011

(86) PCT No.: PCT/EP2011/058035
§ 371 (c)(1),
(2), (4) Date: Jan. 28, 2013

(87) PCT Pub. No.: WO2011/144655
PCT Pub. Date: Nov. 24, 2011

(65) Prior Publication Data
US 2013/0203993 A1    Aug. 8, 2013

(30) Foreign Application Priority Data

May 19, 2010   (EP) .................................... 10163212

(51) Int. Cl.
| | | |
|---|---|---|
| *C07D 403/00* | (2006.01) | |
| *C07C 241/04* | (2006.01) | |
| *C07C 243/28* | (2006.01) | |
| *C07C 251/76* | (2006.01) | |
| *C07D 405/06* | (2006.01) | |
| *C07D 405/14* | (2006.01) | |
| *C07F 7/18* | (2006.01) | |
| *C07C 249/16* | (2006.01) | |

(52) U.S. Cl.
CPC ............ *C07C 241/04* (2013.01); *C07C 243/28* (2013.01); *C07C 249/16* (2013.01); *C07C 251/76* (2013.01); *C07D 405/06* (2013.01); *C07D 405/14* (2013.01); *C07F 7/188* (2013.01); *C07F 7/1852* (2013.01)

(58) Field of Classification Search
CPC ................................ C07F 7/18; C07C 251/76
USPC ......................................................... 544/366
See application file for complete search history.

(56) References Cited

U.S. PATENT DOCUMENTS

| | | |
|---|---|---|
| 4,957,730 A | 9/1990 | Bohn et al. |
| 5,403,937 A | 4/1995 | Saksena et al. |
| 5,486,625 A | 1/1996 | Leong et al. |
| 5,595,872 A | 1/1997 | Wetterau |
| 5,693,626 A | 12/1997 | Saksena et al. |
| 5,710,154 A | 1/1998 | Saksena et al. |
| 5,714,490 A | 2/1998 | Saksena et al. |
| 5,834,472 A | 11/1998 | Sangekar et al. |
| 5,972,381 A | 10/1999 | Sangekar et al. |
| 6,355,801 B1 | 3/2002 | Giesinger et al. |
| 6,958,337 B2 | 10/2005 | Andrews et al. |
| 2010/0197621 A1 | 8/2010 | Henry |

FOREIGN PATENT DOCUMENTS

| | | |
|---|---|---|
| EP | 0736030 A1 | 10/1996 |
| EP | 1230231 B1 | 8/2002 |
| EP | 01394162 | 3/2004 |
| WO | 9309114 | 5/1993 |
| WO | 9425452 A1 | 11/1994 |
| WO | 9516658 A1 | 6/1995 |
| WO | 9517407 A1 | 6/1995 |
| WO | WO 9517407 A1 * | 6/1995 |
| WO | 2006007540 | 1/1996 |
| WO | 9633163 | 10/1996 |

(Continued)

OTHER PUBLICATIONS

Blundell et al., Synlett 1994, pp. 263-265.
Brown et al., J. Chem. Soc. 2003, 125 (36), 10808-10809.
Cordova et al., Chem. Eur. J. 2004, 10 (15), 3673-3684.
Di Santo et al., "antifungal estrogen-like imidazoles. Synthesis and antifungal activities of thienyl and 1H-pyrrolyl derivatives of 1-aryl-2-(1H-imidazol-1-yl)ethane", European Journal of Medicinal Chemistry, Editions Scientifique Elsevier, Paris, FR, vol. 32, No. 2, Jan. 1, 1997, pp. 143-149.

(Continued)

*Primary Examiner* — Porfirio Nazario Gonzalez
*Assistant Examiner* — Kofi Adzamli
(74) *Attorney, Agent, or Firm* — Jeffrey S. Melcher; Manelli Selter PLLC

(57) ABSTRACT

The present invention relates to a process for the preparation of a chiral compound according to formula (V) wherein $R_1$ is preferably an alkyl residue preferably having from 1 to 6 carbon atoms, in particular to a process for the preparation of a chiral compound the crystalline chiral compounds as such, and their use for the preparation of an antifungal agent, in particular posaconazole.

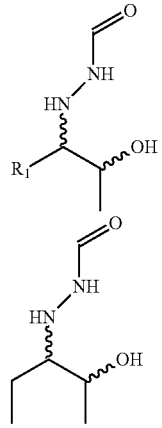

(V)

35 Claims, 2 Drawing Sheets

(56) References Cited

FOREIGN PATENT DOCUMENTS

Figure 1:
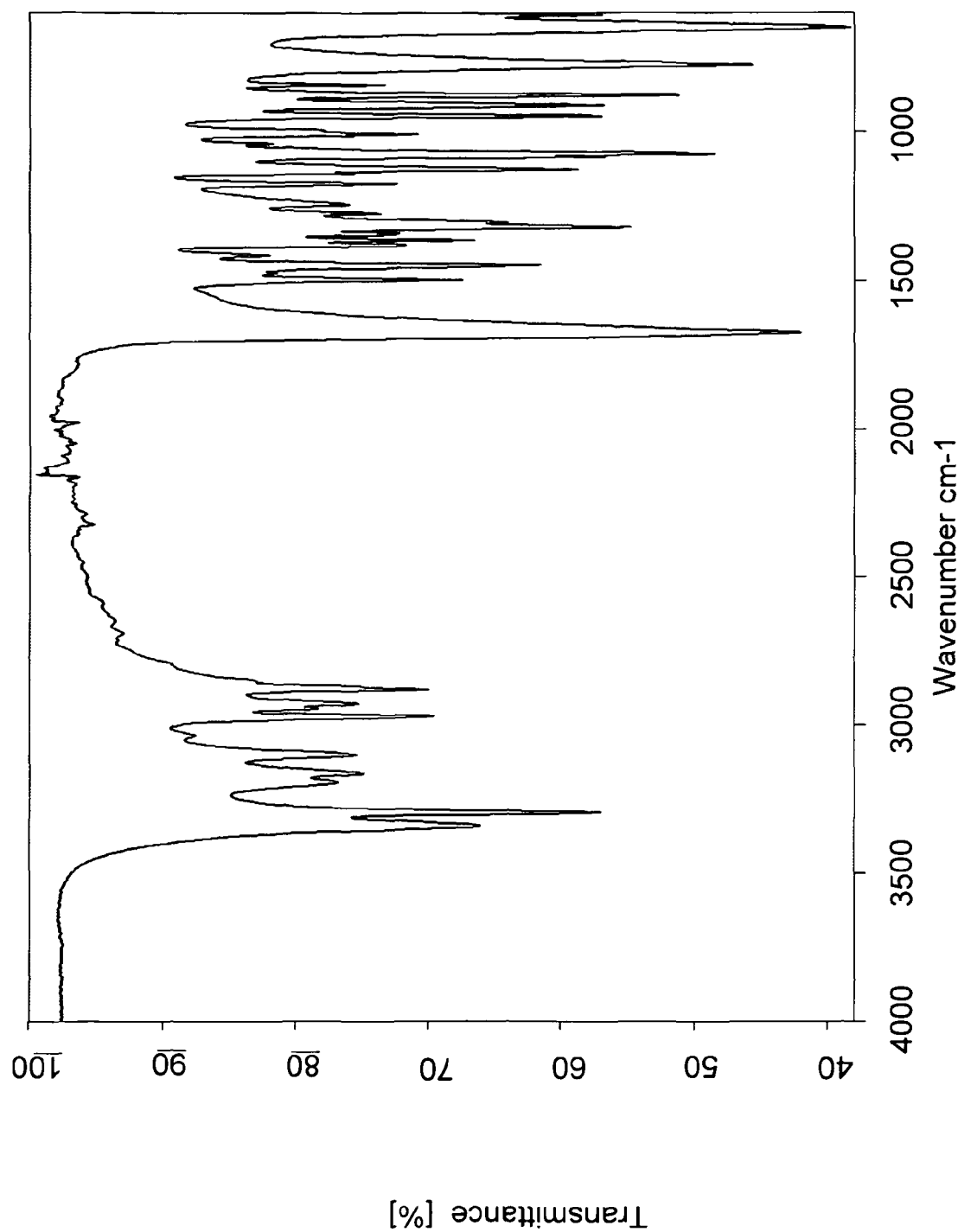

| WO | 9633178 | 10/1996 |
|---|---|---|
| WO | 9638443 | 12/1996 |
| WO | 9700255 A1 | 1/1997 |
| WO | 9722579 | 6/1997 |
| WO | 9722710 A1 | 6/1997 |
| WO | 9733178 | 9/1997 |
| WO | 9918097 | 4/1999 |
| WO | 02080678 | 10/2002 |
| WO | 2005/075473 | 1/2005 |
| WO | 2005117831 | 12/2005 |
| WO | 2007/122156 | 4/2007 |
| WO | 2007/143390 | 12/2007 |
| WO | 2008/136279 | 4/2008 |
| WO | 2009/058267 | 5/2009 |
| WO | 2009/141837 | 5/2009 |
| WO | 2009/129297 | 10/2009 |
| WO | 2010000668 | 1/2010 |
| WO | 2011/144653 | 11/2011 |
| WO | 2011/144656 | 11/2011 |
| WO | 2011/144657 | 11/2011 |
| WO | 2013/186320 | 12/2013 |

OTHER PUBLICATIONS

Greene et al., Protective Groups in Organic Synthesis:, 2nd ed., John Wiley & Sons, New York 1991 10-142.
Greene et al., Protective Groups in Organic Synthesis:, 3rd ed., Wiley-Interscience (1999).
Hayashi et al., J. Org. Chem. 2005, 69 (18), 5966-5973.
Hepperle et al., Tetrahedron Lett. 2002, 43, 3359-3363.
Huang et al., Organic Letters 2004, 6 (25) 4795-4798.
Kurome et al., "Total Synthesis of an Antifungal Cyclic Depsipeptide Aureobasidin A", Tetrahedron, Elsevier Science Publishers. Amsterdam, NL, vol. 52, No. 12. Mar. 18, 1996, pp. 4327-4346.
Na Y-M et al., "Synthesis and antifungal activity of new 1-halogenbenzyl-3-imidazoly 1methylindole derivatives", European Journal of Medicinal Chemistry, Editions Scientifique Elsevier, Paris, FR, vol. 38, No. 1, Jan. 1, 2003, pp. 75-87.
Peterson, "Carbonyl olefination reaction using silyl-substituted organometallic compounds", J. Org. Chem (1968) 33 (2) pp. 780-784.
Remington's Pharmaceutical Sciences, 15th Ed., Mack Publishing Co., New Jersey (1991).
Saksena et al., Tetrahedron Lett. 2004, 45 (44), 8249-8251.
Tetrahedron Letters 32 (1991). pp. 7545-7548.
Xianhai Huang et al., "Manipulation of N,O-Nucleophilicity: Efficient Formation of 4-N-Substituted 2,4-Dihydro-3H-1, 2, 4-Triazolin-3-ones", Organic Letters, American Chemical Society, US, vol. 6, No. 25, Nov. 10, 2004, pp. 4795-4798.
International Search Report and Written Opinion Mailed Sep. 9, 2011 in PCT/EP2011/058035.
International Search Report and Written Opinion Mailed Aug. 4, 2011 in PCT/EP2011/058036.
International Search Report and Written Opinion Mailed Aug. 5, 2011 in PCT/EP2011/058039.
International Search Report and Written Opinion Mailed Jul. 13, 2011 in PCT/EP2011/058033.
Weicheng Thou et al., Survey of Syntheses of Azole Antifungals. Chinese Journal of Pharmaceuticals, vol. 37, No. 2, pp. 125-133, Dec. 31, 2006.
Sixi Wang, Synthesis of SIPI-4678 and Voriconazole, The Master Degree Theses of the Shanghai Institute of Parmaceutical Industry, pp. 10-13, Mar. 2007.
Sixi, Wang, Synthesis of SIPI-4678 and Voriconazole, The Master Degree Theses of the Shanghai Institute of Pharmaceutical Industry, pp. 9-17, Jan. 24, 2007.
Chinese Office Action issued in Application No. 201180024340.2, Mar. 24, 2014, pp. 1-13, and translation.
Chinese Office Action issued in Application No. 201180024363.3, Jan. 17, 2014, pp. 1-7, and translation.
Chinese Office Action issued in Application No. 201180024632.6, May 20, 2014, pp. 1-10, and translation.
Parmee, "Human beta3 adreneergic receptor containing cyclic ureidobenzenesulonafides," Bioorganic & Medicinal Chemistry Letters, vol. 9, 1999, pp. 749-745, XP002648199.
International Preliminary Report on Patentability issued in PCT/EP2012/061346, WO2012/172015, Oct. 9, 2013, pp. 1-8.
International Search Report issued in PCT/EP2012/061346, WO2012/172015, Aug. 1, 2012, pp. 1-9.
Written Opinion issued in PCT/EP2012/061346, WO2012/172015, Jun. 20, 2013, pp. 1-5.
International Preliminary Report on Patentability issued in PCT/EP2012/061346, WO2012/172015, Jun. 3, 2014, pp. 1-29.
International Search Report issued in PCT/EP2013/062298, WO2013/186320, Feb. 8, 2013, pp. 1-4.
Written Opinion issued in PCT/EP2013/062298,WO2013/186320, Feb. 8, 2013, pp. 1-13.
Brown et al., J. Chem. Am. Soc. 2003, 125 (36), 10808-10809.
Robert V. Hoffman, Organic Chemistry: An Intermediate Text, Second Edition, John Wiley & Sons, Inc., 2004, p. 128.
Hacker, "Aromatic 2-(Thio)ureidocarboxylic Acids as New Family of Modulators of Multidrug Resistance-Associated Protein 1: Synthesis, Biological Evaluation, and Structure-Activity Relationships," Journal of Medicinal Chemistry, 2009, vol. 52, No. 15, pp. 4587-4593.
Office Action issued in Chinese Patent Application Serial No. 2011800243402, Dec. 8, 2014, pp. 1-13, translation included.
Serajuddin, Abu. Advanced Drug Delivery Reviews 59 (2007) pp. 603-616.
Reichardt, Chr. Solvents and Solvent Effects in Organic Chemistry. 3rd ed. Wiley-VCH. (2004) pp. 418-421.
Saksena, Anil K.; Girijavallabhan, Viyyoor M.; Lovey, Raymond G.; Pike, Russell E.; Wang, Haiyan; Ganguly, Ashit K.; Morgan, Brian; Zaks, Alesey; Puar, Mohinder S., Highly stereoselective access to novel 2,2,4-trisubstituted tetrahydrofurans by halocyclization: practical chemoenzymic synthesis of SCH 51048, a broad-spectrum orally active antifungal agent, Tetrahedron Letters, 1995, 36(11), pp. 1787-1790.
Konosu, Toshiyuki; Tajima, Yawara; Miyaoka, Takeo; Oida, Sadao, Concise synthesis of optically active oxirane precursors for the preparation of triazole antifungals using the Friedel-Crafts reaction of (S)-2-tosyloxypropionyl chloride, Tetrahedron Letters, 1991, 32(51), pp. 7545-7548.
The Chemical Society of Japan, Handbook of Chemistry, Applied Chemistry 6th Ed., Maruzen, Jan. 30, 2003, p. 178.
Japanese Office Action issued Mar. 3, 2015, in Japanese Patent Application No. 2013-510614, pp. 1-6.

\* cited by examiner

PROCESS FOR THE PREPARATION OF CHIRAL HYDRAZIDES

The present invention relates to a process for the preparation of a chiral compound, in particular to a process for the preparation of a chiral compound which may be used as intermediate for the preparation of antifungal agents, preferably posaconazole.

BACKGROUND PRIOR ART

Posaconazole (CAS Registry Number 171228-49-2; CAS Name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl] phenoxy]methyl]-1-(1H-1,2,4-triazol-1-yl)-D-threo-pentitol) is a triazole antifungal drug represented by the structure:

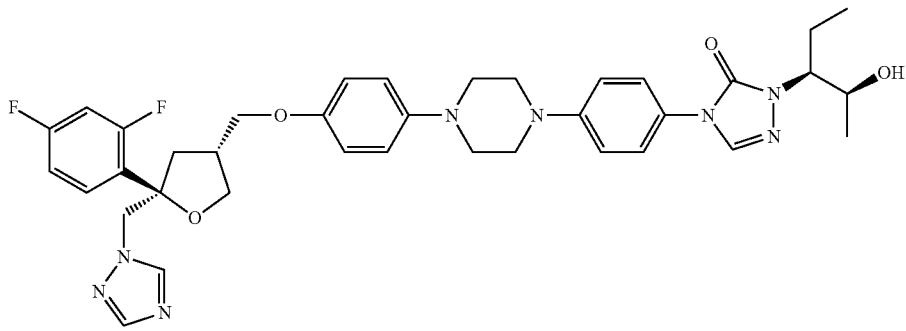 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

Posaconazole is used, for example, to prevent and/or treat invasive fungal infections caused by *Candida* species, *Mucor* species, *Aspergillus* species, *Fusarium* species, or *Coccidioides* species in immunocompromised patients and/or in patients where the disease is refractory to other antifungal agents such as amphothericin B, fluconazole, or itraconazole, and/or in patients who do not tolerate these antifungal agents. One of the important intermediates for the preparation of posaconazole is the compound of formula (V)

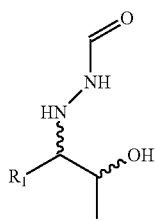

(V)

in particular the compound of formula (V) with $R_1$=ethyl

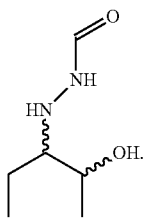

To date, no process has been known which affords the compound of formula (V), in particular the compound of formula (V) with $R_1$=ethyl, especially in high enantiomeric, diastereomeric purity and yield. Only the corresponding benzyl protected compound shown below has been described in the literature until now. Unfortunately, the compound of formula (V) with $R_1$=ethyl is not readily accessible via deprotection of the benzyl protected derivative using standard hydrogenolytic conditions.

A common intermediate in the process for preparing posaconazole is a compound of formula

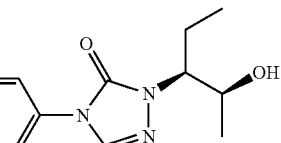

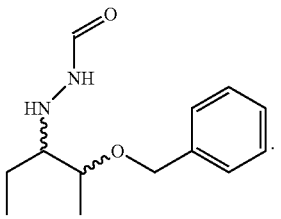 [SMILES: CCC(NNC=O)C(C)OCc1ccccc1]

A process for the preparation of this intermediate is disclosed in WO 95/17407. The overall yield of this process is approximately 25%, and the diastereomeric purity with regard to the isomer of formula

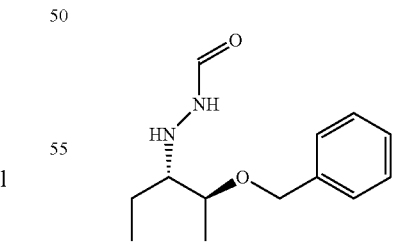

is in the range of from 94-99%, with the enantiomeric purity depending on the quality of the starting material lactic methyl ester. WO 95/17407 is completely silent on a purification of said intermediate.

WO 97/22579 and Saksena et al., *Tetrahedron Lett.* 2004, 45 (44), 8249-8251, disclose improved processes for the Grignard reaction carried out in the course of the reaction sequence described in WO 95/17407. A silylation step and addition of tert-BuMgCl to the Grignard reaction is described to afford the intermediate with a purity of 95% without using an additional purification by chromatography. However, the inventors of the present invention, although high-skilled technical experts in this specific chemical area, were not able to reproduce these results. No matter which reasonable modification of the teaching of WO 97/22579 and Saksena et al. was made, the intermediate was always obtained as a complicated mixture which had to be subjected to double chromatography in order to reach the claimed purity.

A further process disclosed in WO 96/33163 involves stereochemical resolution of an intermediate via salt formation using chiral acids (e.g. dibenzoyl-L-tartaric acid, L-DBTA) and crystallization of the obtained diastereomeric salts in order to obtain the above-described intermediate in high optical purity. Yet another process, disclosed in WO 97/33178, requires protection of one hydrazine nitrogen in order to introduce the chiral center by reduction with costly reagents with a selectivity of 0-94% with regard to the desired isomer. Neither in WO 96/33163 nor in WO 97/33178 a purification of the products is described, except for the stereochemical resolution.

All these methods of the prior art suffer from significant drawbacks.

First, the described approaches share the requirement of an OH protecting group both during the synthesis of an intermediate hydrazide and for the subsequent preparation of antifungal agents. In addition, harsh reaction conditions along the synthesis pathways may be regarded as being prohibitive for widely used protecting groups, including silyl ethers and esters. It is believed that solely ethers are stable enough which may be the reason why in all concrete examples, only benzyl ether is consistently disclosed.

Second, none of these processes of the prior art allows for a direct preparation of an unprotected compound of formula (V) and, for example, a subsequent protection of the OH group of the compound of formula (V) with a desired protecting group tailor-made for subsequent reactions.

Third, as mentioned above, elaborate purification of the oily products by either chromatography or stereochemcial resolution is required to counterbalance the insufficient chemo selectivity and stereoselectivity of the reaction pathways of the prior art.

Fourth, multiple oxidation state adjustments on the reaction pathways of the prior art, including a large excess of expensive reagents, increase the number of individual steps and lower the overall yield. These shortcomings considerably decrease the yield of the desired hydrazide of formula (V) and in particular of formula (V) with R$_1$=ethyl

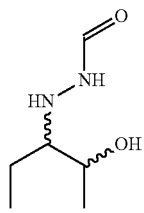

and respectively protected derivatives thereof. At the same time large amount of undesired waste products are obtained, making the prior art process even more disadvantageous.

Therefore, it was an object of the present invention to provide an efficient process for the production of chiral hydrazides, in particular for the production of a compound of formula (V) with R1=ethyl

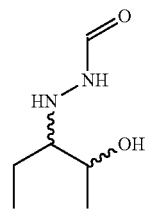

which may be advantageously used as intermediate for the production of azole antifungal agents, in particular posaconazole.

It was a further object of the present invention to provide an efficient process for the preparation of a crystalline compound of formula (V) and in particular of formula (V) with R$_1$=ethyl

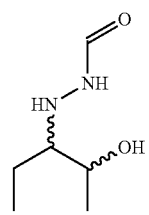

and, further, for compounds based on this crystalline compound suitably protected at the OH group.

It was a further object of the present invention to provide said crystalline compound as such, as well as said suitably protected compounds.

Surprisingly, it was found that above-discussed objects are met by a process wherein, in a first stage, a compound of formula

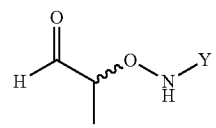

with Y being an optionally substituted aryl moiety is provided and reacted with H$_2$N—NH—CHO in a suitable solvent from which a chiral compound of formula

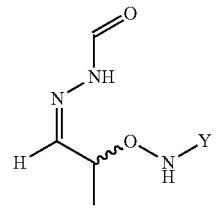

is obtained.

SUMMARY OF THE INVENTION

The present invention relates to a process for the preparation of a chiral compound, comprising
(1) providing a chiral compound of formula (I)

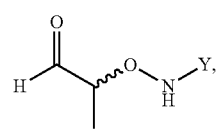

(I)

wherein Y is an optionally substituted aryl moiety, preferably an optionally substituted phenyl moiety, more preferably unsubstituted phenyl;

(2) reacting the compound of formula (I) with H$_2$N—NH—CHO in a solvent to obtain a compound according to formula (II)

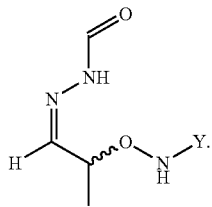
(II)

Further, the present invention relates to a process for the preparation of a chiral compound, comprising
(1) providing a chiral compound of formula (I)

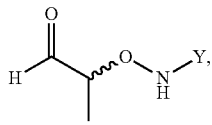
(I)

wherein Y is an optionally substituted aryl moiety, preferably an optionally substituted phenyl moiety, more preferably unsubstituted phenyl;
(2) reacting the compound of formula (I) with H$_2$N—NH—CHO in a solvent to obtain a compound according to formula (II)

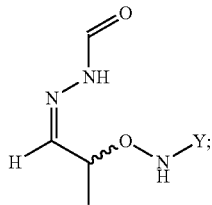
(II)

(3) separating the compound of formula (II) from the reaction mixture obtained from (2) by solvent extraction, wherein prior to (3), a solvent exchange is preferably carried out;
(4) reacting the compound of formula (II) in a solvent with a silylating agent comprising the residue —SiR$_{aa}$R$_{bb}$R$_{cc}$ to obtain a compound of formula (III)

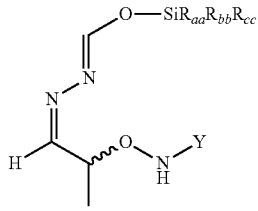
(III)

wherein the residues R$_{aa}$, R$_{bb}$ and R$_{cc}$ may be the same or different and are preferably alkyl or aryl residues, more preferably alkyl residues having from 1 to 6 carbon atoms, preferably from 1 to 4 carbon atoms, more preferably 1 or 2 carbon atoms;
(5) reacting the compound of formula (II) or reacting the compound of formula (III) with a nucleophilic compound comprising a nucleophilic residue R$_1$ in a solvent to obtain a compound of formula (IV)

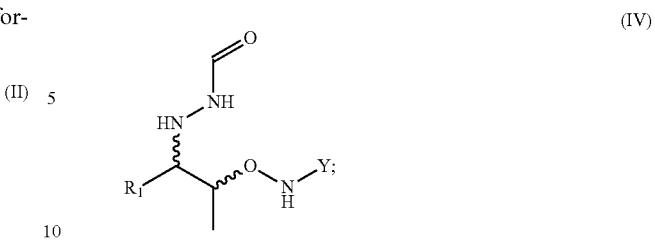
(IV)

(6) reducing the compound of formula (IV), preferably by hydrogenation, to obtain a compound of formula (V)

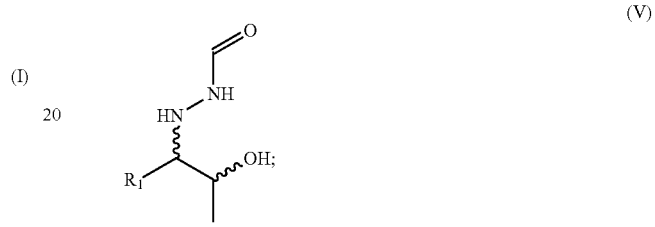
(V)

(7) optionally reacting the compound of formula (V) in a solvent with a silylating agent comprising the residue —SiR$_a$R$_b$R$_c$ to obtain a compound of formula (VI)

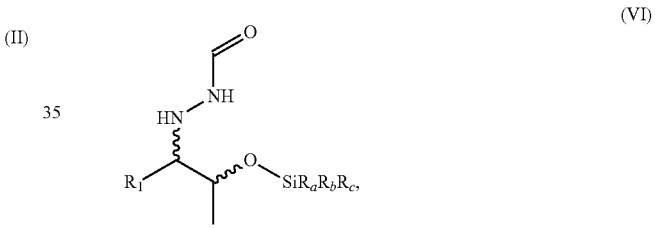
(VI)

wherein the residues R$_a$, R$_b$ and R$_c$ may be the same or different and are preferably alkyl or aryl residues.

The present invention further relates a chiral compound which is obtainable or obtained by the process of the present invention.

In particular, the present invention relates to a preferably crystalline chiral compound according to formula (V) wherein R$_1$ is preferably an alkyl residue preferably having from 1 to 6 carbon atoms, more preferably from 1 to 4 carbon atoms, more preferably 1 or 2 carbon atoms, most preferably 2 carbon atoms, R$_1$ in particular being ethyl, wherein preferably at least 95%, preferably at least 97%, more preferably at least 99% of the molecules of said crystalline compound are present as isomer of formula (Va)

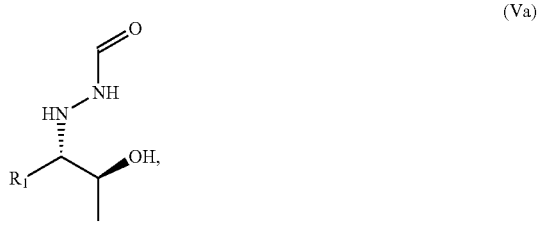
(Va)

in particular as isomer of formula (Vb)

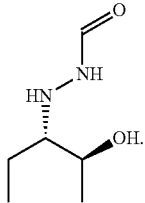
(Vb)

Further, the present invention also relates to the use of a chiral compound according to the present invention, in particular a compound of formula (Vb), for the preparation of an antifungal agent, in particular for the preparation of posaconazole.

SHORT DESCRIPTION OF THE FIGURES

FIG. 1 shows the infrared spectrum (IR) of the compound of formula (V) as obtained according to Example 3 of the present invention. In FIG. 1, transmittance in % is presented on the y-axis, while wavenumber $cm^{-1}$ is presented on the x-axis.

The following IR peaks can be seen in particular:

3341, 3298, 2970, 2881, 1674, 1497, 1447, 1319, 1125, 1071, 945, 910, 876, 775 and 650+/−2 $cm^{-1}$.

Figure 2:
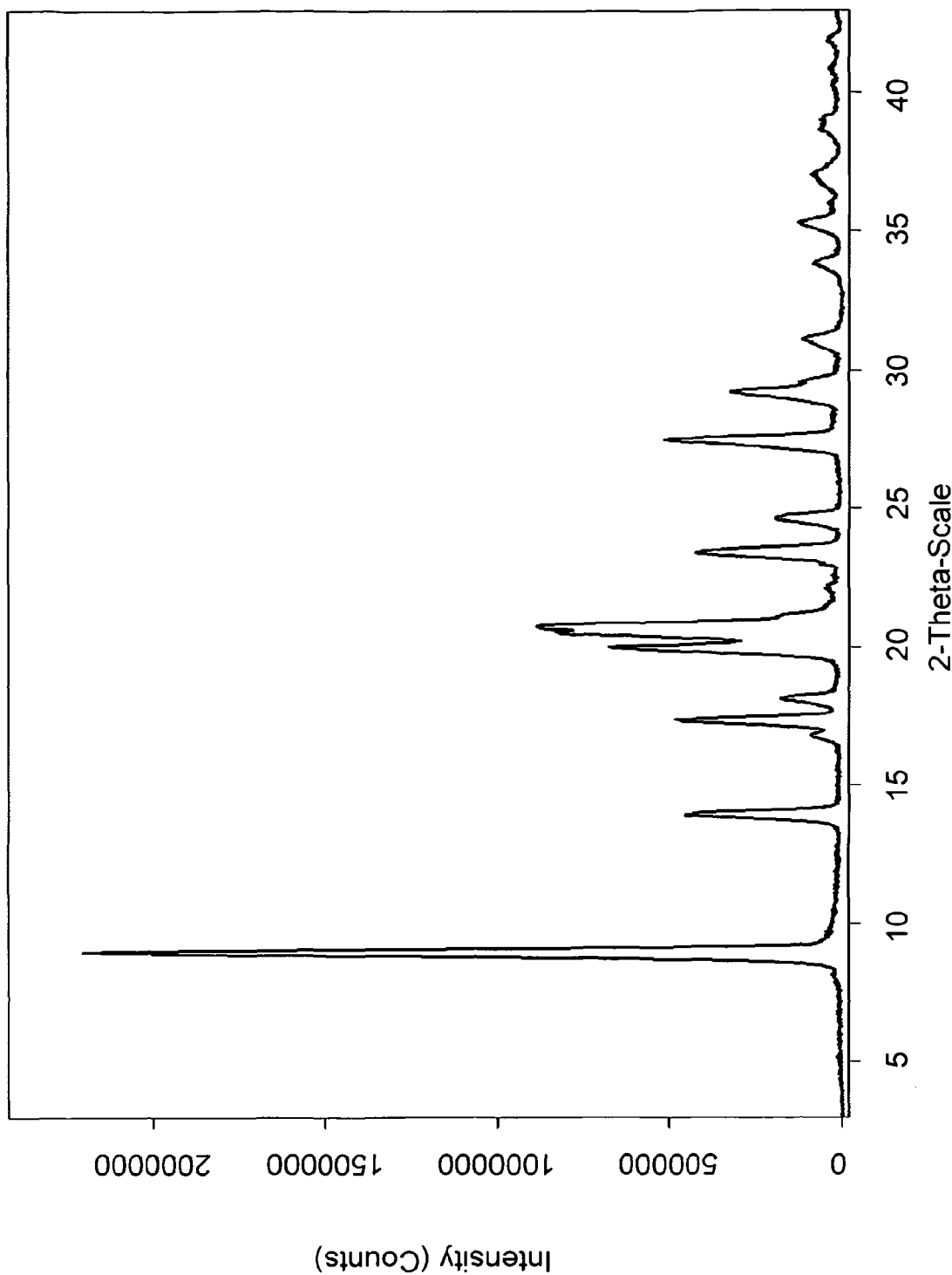

FIG. 2 shows the X-ray diffractogram of the compound of formula (V) as obtained according to Example 3 of the present invention. In FIG. 2, intensity—measured as counts per 300 seconds (linear scale)—is presented on the y-axis, while the position—expressed as 2 theta values in degrees—is presented on the x-axis.

The following XRD peaks can be seen in particular:

9.0, 13.9, 17.4, 18.1, 20.0, 20.7, 23.4, 24.6, 27.5 and 29.2+/−0.2° 2-Theta.

DETAILED DESCRIPTION

As mentioned above, the present invention relates to a process for the preparation of a chiral compound, comprising (1) providing a chiral compound of formula (I)

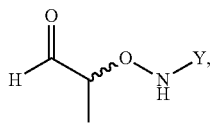
(I)

wherein Y is an optionally substituted aryl moiety, preferably an optionally substituted phenyl moiety, more preferably unsubstituted phenyl;

(2) reacting the compound of formula (I) with H₂N—NH—CHO in a solvent to obtain a compound according to formula (II)

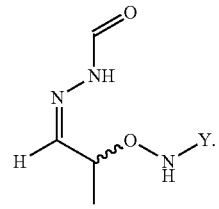
(II)

Step (1)

According to step (1) of the present invention, a compound of formula (I) is provided which is reacted in step (2) with H₂N—NH—CHO in a suitable solvent.

Generally, there are no specific restrictions as far as providing the compound of formula (I) is concerned. In particular, every conceivable method for the preparation of the compound of formula (I) may be carried out. According to a preferred embodiment of the present invention, such methods are preferred which allow for the preparation of a compound of formula (I) with high enantioselectivity. According to an even more preferred embodiment of the present invention, such methods are preferred which allow for the preparation of compound (I) wherein at least 95%, more preferably at least 97%, more preferably at least 99% of the molecules of the chiral compound of formula (I) provided in (1) are present as isomer of formula (Ia)

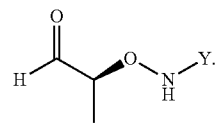
(Ia)

For Y=phenyl, the preparation of the compound of formula (I) in an organocatalytic reaction with excellent enantioselectivity is known. Reference is made to Brown et al., *J. Chem. Soc.* 2003, 125 (36), 10808-10809 and Cordova et al., *Chem. Eur. J.* 2004, 10 (15), 3673-3684; as well as Hayashi et al. *J. Org. Chem.* 2005, 69 (18), 5966-5973.

According to a preferred embodiment, the compound of formula (I) is provided according to the present invention by reacting propionaldehyde in a suitable solvent with a compound of formula (i)

(i).

Residue Y of the compound of formula (i) is an optionally substituted aryl moiety, preferably an optionally substituted phenyl moiety, more preferably unsubstituted phenyl. The term "aryl moiety" as used in this context of the present invention relates to a carbocyclic aromatic group, such as phenyl or naphthyl or the like. The term "substituted aryl moiety" and "substituted phenyl", respectively, as used in this context of the present invention relates to such aryl moiety and phenyl, respectively, which preferably bears one, two, or three substituents which are preferably selected from the group consisting of halo, alkyl, and $C_1$ alkoxy or $C_2$ alkoxy or $C_3$ alkoxy or $C_4$ alkoxy or $C_5$ alkoxy or $C_6$ alkoxy.

The term "alkyl" as used in the context of the present invention relates to straight or branched alkyl moieties which preferably have 1, 2, 3, 4, 5, or 6 carbon atoms. The term "halo" as used in this context of the present invention in particular relates to a chlorine, a bromine, or a iodine atom.

Therefore, in particular, residue Y of the compound of formula (i) is not a benzyl moiety, in particular not an alkylaryl moiety. The term "alkylaryl" moiety as used in the context of the present invention relates to an alkyl moiety which is substituted by at least one aryl moiety. For the sake of illustration, the benzyl moiety is an alkylaryl moiety, wherein alkyl is methyl which is substituted by one phenyl moiety.

Thus, according to a preferred embodiment of the present invention, the compound of formula (i) is nitrosobenzene.

As far as the reaction of propionaldehyde with the compound of formula (i) is concerned, no specific restrictions exist with the proviso that the compound of formula (I) is obtained, preferably a compound (I) wherein at least 95%, more preferably at least 97%, more preferably at least 99% of the molecules of the chiral compound of formula (I) provided in (1) are present as isomer of formula (Ia)

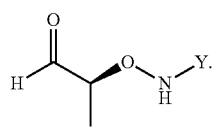
(Ia)

Preferably, at least one, preferably exactly one organocatalyst is employed in the reaction for providing the compound of formula (I). More preferably, proline (Pro), even more preferably D-proline (D-Pro)

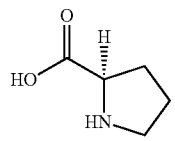

is employed as organocatalyst.

According to an optional embodiment of the present invention, at least one suitable promoter may be employed for promoting the reaction, preferably the organocatalyzed reaction in step (1). While every conceivable promoter can be used, preference is given in the context of the present invention to a urea derivative, with 1-(2-dimethylamino-ethyl)-3-phenyl urea being especially preferred.

It was found that carrying out this reaction in the presence of an acid is even more preferred. While generally, no specific restrictions may exist, preference is given to Bronstedt acids, in particular organic Bronstedt acids. According to still further preferred embodiments, acetic acid or propionic acid or a mixture of these acids is employed. No specific restrictions exist as far as the amount of the acids employed is concerned. Catalytical amounts are preferred. Compared to the amounts of the organocatalyst employed, it is even more preferred to employ the acid in a lower amount. According to conceivable embodiments, and based on 1 equivalent of the compound of formula (i), the amount of organocatalyst may be in the range of from 0.15 to 0.5, more preferably in the range of from 0.2 to 0.4, more preferably in the range of from 0.25 to 0.35 equivalents, and the amount of acid may be in the range of from 0.01 to 0.1, more preferably in the range of from 0.02 to 0.09, more preferably in the range of from 0.03 to 0.08 equivalents.

The chemical nature of the suitable solvent in which the reaction according to step (1) is carried out will principally depend on the specific starting materials, the catalyst or catalysts employed, the acid or the acids, if employed, and/or the promoter or the promoters being present, if employed. One solvent or a mixture of two or more solvents is conceivable. According to a preferred embodiment of the present invention wherein propionaldehyde is reacted with nitrosobenzene in the presence of D-Pro and in the presence of acetic acid and/or propionic acid, the reaction is preferably carried out in dichloromethane (DCM) as solvent.

The temperature at which the reaction according to step (1) is carried out will principally depend on the specific starting materials, the catalyst or catalysts employed, the acid or the acids, if employed, and/or the promoter or the promoters being present, if employed. According to a preferred embodiment of the present invention, in particular wherein propionaldehyde is reacted with nitrosobenzene in the presence of D-Pro and in the presence of acetic acid and/or propionic acid in DCM as solvent, the reaction is preferably carried out at a temperature in the range of from −15 to +5° C., preferably from −12 to +3° C., more preferably from −10 to 0° C.

The atmosphere under which the reaction for providing the compound of formula (I) is carried out will generally depend on the specific starting materials, the solvent or solvents used, the catalyst or catalysts employed, the acid or the acids, if employed, and/or the promoter or the promoters being present, if employed. According to a preferred embodiment of the present invention wherein propionaldehyde is reacted with nitrosobenzene in the presence of D-Pro, the reaction is carried out under inert or essentially inert atmosphere, such as in $N_2$ atmosphere.

Thus, from the reaction carried out in step (1), the compound of formula (I) is preferably obtained in at least one solvent, preferably DCM, wherein at least 95%, more preferably at least 97%, more preferably at least 99% of the molecules of the chiral compound of formula (I) provided in (1) are present as isomer of formula (Ia)

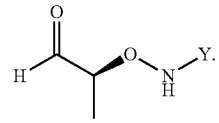
(Ia)

Step (2)

Generally, it is conceivable to separate the compound of formula (I) from the reaction mixture obtained from step (1). However, according to a particularly preferred embodiment of the present invention, no such separation is necessary. Therefore, the present invention also relates to above-described process wherein after (1), the compound of formula (I) is not separated from the reaction mixture obtained from (1) prior to reaction with $H_2N-NH-CHO$ in (2).

Thus, according to a conceivable embodiment, the reaction mixture obtained from step (1) may be employed in step (2) as such. Alternatively, the reaction mixture may be further diluted with at least one suitable solvent, or, if desired, a suitable amount of solvent may be removed from the reaction mixture by suitable concentration.

According to step (2) of the present invention, the compound of formula (I) is reacted with $H_2N-NH-CHO$ in a solvent. This solvent may be a solvent mixture if, for example, the reaction mixture obtained from step (1) is admixed with $H_2N-NH-CHO$ (formyl hydrazine) contained in a solvent which is different from the solvent contained in the reaction mixture obtained from step (1). According to an especially preferred embodiment of the present invention, the solvent which is contained in the reaction mixture obtained from step (1) is the same solvent which is used for carrying out the reaction in step (2). In particular, this solvent is DCM.

As for the reaction in step (1), the temperature at which the reaction according to step (2) is carried out will principally depend on the specific compounds to be reacted with each other, the catalyst or catalysts employed, the acid or the acids, if employed, and/or the promoter or the promoters being present, if employed. According to a preferred embodiment of the present invention, in particular wherein propionaldehyde has been reacted with nitrosobenzene in the presence of D-Pro and in the presence of acetic acid and/or propionic acid in DCM as solvent in step (1), and if also the reaction in step (2) is carried out in DCM as solvent, the reaction in step (2) is preferably carried out at a temperature in the range of from −10 to +20° C., preferably from −5 to +5° C.

Preferably, the reaction in step (2) is carried out in the presence of at least one molecular sieve. The characteristics of the at least one molecular sieve with respect to the pores can be adapted to the specific needs. However, such sieves are preferred which have pore diameters, determined according to DIN 66131, in the range of from 0.3 to 0.5 nm (nanometre; 3 to 5 Angstrom), preferably from 0.35 to 0.45 nm (3.5 to 4.5 Angstrom), with a pore diameter of about 0.4 nm (4 Angstrom) being especially preferred.

The atmosphere under which the reaction in step (2) for providing the compound of formula (II) is carried out will, again, generally depend on the specific compounds to be reacted with each other, the solvent or solvents used, the catalyst or catalysts employed, the acid or the acids, if employed, and/or the promoter or the promoters being present, if employed. According to a preferred embodiment of the present invention wherein propionaldehyde has been reacted with nitrosobenzene in the presence of D-Pro and in the presence of acetic acid and/or propionic acid in DCM as solvent in step (1), and if also the reaction in step (2) is carried out in DCM as solvent, the reaction in step (2) is carried out under inert or essentially inert atmosphere, such as in $N_2$ atmosphere.

Step (3)

From the reaction mixture obtained from step (2), the compound of formula (II) may be separated. While there are no specific restrictions as to how such separation is carried out, solvent extraction is a preferred method according to the present invention. Prior to such extraction, a suitable solvent exchange is preferably carried out. As far as the solvent exchange is concerned, it is especially preferred to exchange the solvent in which the compound of formula (II) is obtained according to step (2) by a solvent or a mixture of two or more solvents which is/are suitable for a preferred further stage of the present invention, such as reaction step (4) described in detail hereinunder. The specific type of solvent will depend on the specific compound of formula (II) and the specific type of subsequent reaction. In case the subsequent reaction is the reaction described hereinunder in step (4), and in case the compound of formula (II) is employed in step (3) preferably contained in DCM, it is preferred to exchange this solvent by MTBE (methyl-tert-butyl ether), ethyl acetate, or a mixture of MTBE and ethyl acetate. Especially preferred is MTBE.

According to the present invention, preferred extracting agents are selected from the group consisting of water preferably containing at least one suitable salt, organic ethers, organic esters, and a mixture of two or more thereof, wherein said salt is preferably selected from the group consisting of sodium chloride, sodium hydrogencarbonate, and ammonium chloride. More preferably, the extracting agent is water containing at least one suitable salt, preferably containing one suitable salt, more preferably containing sodium chloride. As far as the amount of salt contained in the water is concerned, typical embodiments are aqueous solutions containing 10 to 30 wt.-% of salt.

Further, it is conceivable to suitably crystallize the compound of formula (II) obtained from step (3). No specific restrictions exist as far as such crystallization is concerned with the proviso that at least a portion of the compound of formula (II) crystallizes.

Therefore, the present invention also relates to the optionally crystalline compound of formula (II) as such

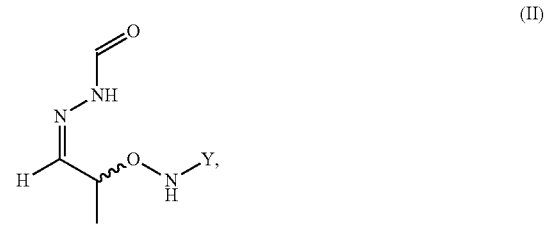

(II)

wherein Y is an optionally substituted aryl moiety, preferably an optionally substituted phenyl moiety, more preferably unsubstituted phenyl, wherein preferably at least 95%, more preferably at least 97%, more preferably at least 99% of the molecules of said optionally crystalline compound are present as isomer of formula (IIa)

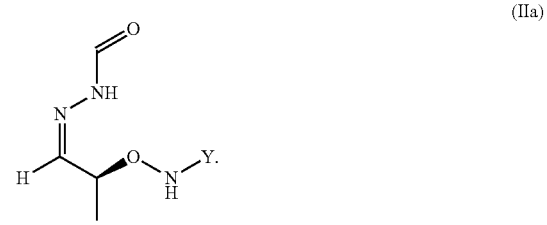

(IIa)

In particular, the present invention relates to the optionally crystalline compound of formula (II) with Y=phenyl, wherein at least 99% of the molecules of said optionally crystalline compound are present as isomer of formula (IIb)

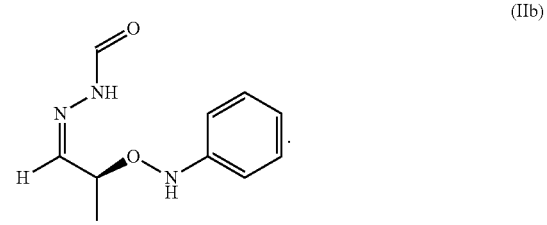

(IIb)

An advantage of the process of the present invention is to be seen in the fact that steps (1), (2), and (3) can be carried out in a single reaction vessel. No complicated transfers of reaction mixtures are necessary, allowing in particular for a simplified large-scale production.

Step (4)

As mentioned above, an aqueous salt solution can be employed as extracting agent. Therefore, prior to a subsequent reaction step it may be desired to remove remaining water from the mixture obtained from solvent extraction. For such water removal, it is possible according to the present invention to employ at least one molecular sieve. The characteristics of the at least one molecular sieve with respect to the pores can be adapted to the specific needs. However, such sieves are preferred which have pore diameters, determined according to DIN 66131, in the range of from 0.3 to 0.5 nm (3 to 5 Angstrom), preferably from 0.35 to 0.45 nm (3.5 to 4.5 Angstrom), with a pore diameter of about 0.4 rim (4 Angstrom) being especially preferred. The water content of the resulting mixtures are most preferably at least 0.1 wt.-%, more preferably at least 0.05 wt.-%.

According to a preferred embodiment of the present invention, the compound of formula (II), preferably contained in the solvent as described above, even more preferably after above-described solvent exchange, in particular contained in MTBE, and optionally after removal of remaining traces of water, is reacted in a step (4) with a silylating agent. Thus, the solvent used for this reaction is most preferably MTBE. From this reaction in step (4), a compound of formula (III) is obtained

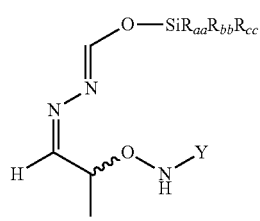

(III)

wherein the residues $R_{aa}$, $R_{bb}$ and $R_{cc}$ may be the same or different and are preferably alkyl or aryl residues, more preferably alkyl residues having from 1 to 6 carbon atoms, preferably from 1 to 4 carbon atoms, more preferably 1 or 2 carbon atoms.

The term "aryl residue" as used in this context of the present invention relates to a carbocyclic aromatic group, such as phenyl or naphthyl or the like. The term "alkyl residue" as used in the context of the present invention relates to straight or branched alkyl moieties which preferably have 1, 2, 3, 4, 5, or 6 carbon atoms. Preferably, the residues $R_{aa}$, $R_{bb}$ and $R_{cc}$ may be the same or different and are alkyl residues. More preferably, the alkyl residues have 1, 2, 3 or 4 carbon atoms, such as methyl, ethyl, propyl or butyl. More preferably, the alkyl residues have 1 or 2 carbon atoms. Even more preferably, the residues $R_{aa}$, $R_{bb}$ and $R_{cc}$ are the same, in particular methyl.

As far as the silylating agents as such are concerned, no particular restrictions exist with the proviso that at least a portion of the compound of formula (II) is silylated to give the compound of formula (III). For the most preferred embodiments of the present invention wherein $R_{aa}$, $R_{bb}$ and $R_{cc}$ are methyl, the most preferred silylating agent is hexamethyldisilazane, trimethylchlorosilane, bistrimethylsilylacetamide or a mixture of two or three of these compounds, preferably bistrimethylsilylacetamide.

The temperature at which the reaction according to step (4) is carried out will principally depend on the specific nature of the compound of formula (III), the specific nature of the silylating agent, and/or the solvent. Preferred temperatures according to the present invention are in the range of from 15 to 70° C.

From the reaction mixture obtained, it is conceivable to suitably crystallize the compound of formula (III) obtained from step (4). No specific restrictions exist as far as such crystallization is concerned with the proviso that at least a portion of the compound of formula (III) crystallizes.

Therefore, the present invention also relates to compound of formula (III) as such

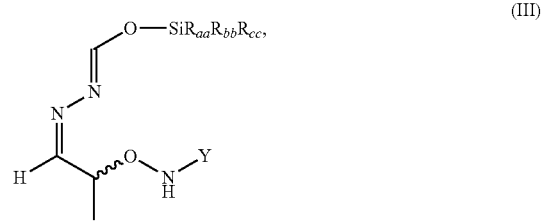

(III)

which, according to a conceivable embodiment, may be at least partially crystalline, wherein Y is an optionally substituted aryl moiety, preferably an optionally substituted phenyl moiety, more preferably unsubstituted phenyl, wherein the residues $R_{aa}$, $R_{bb}$ and $R_{cc}$ may be the same or different and are preferably alkyl or aryl residues, more preferably alkyl residues having from 1 to 6 carbon atoms, preferably from 1 to 4 carbon atoms, more preferably 1 or 2 carbon atoms, in particular methyl, wherein preferably at least 95%, more preferably at least 97%, more preferably at least 99% of the molecules of said chiral compound are present as isomer of formula (IIIa)

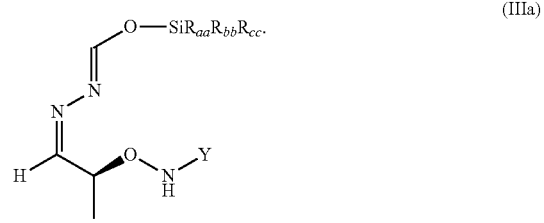

(IIIa)

In particular, the present invention relates to the compound of formula (III) with Y=phenyl, which, according to a conceivable embodiment, may be at least partially crystalline, wherein at least 99% of the molecules of said optionally crystalline compound are present as isomer of formula (IIIb)

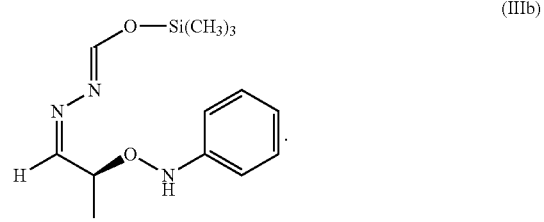

(IIIb)

As mentioned above, according to step (4) of the present invention, the compound of formula (III) is obtained contained in a solvent which is most preferably MTBE. According to this embodiment, the compound of formula (III) is not crystallized. According to an especially preferred embodiment of the present invention, this reaction mixture is subjected without further purification to a further step (5) which is described in detail hereinunder.

'Therefore, the present invention also relates to above-described process wherein after (4), the compound of formula (III) is not separated from the reaction mixture obtained from (4) prior to reaction with the nucleophilic compound in (5).

Step (5)

According to such preferred step (5) of the present invention, the compound of formula (III) is reacted with a nucleophilic compound comprising a nucleophilic residue $R_1$ in a solvent to obtain a compound of formula (IV)

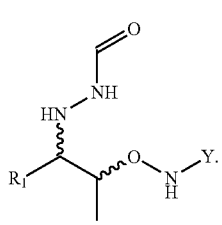

(IV)

According to an alternative conceivable process of the present invention, also the compound of formula (II) as described in detail hereinabove can be reacted with a nucleophilic compound comprising a nucleophilic residue $R_1$ in a solvent to obtain a compound of formula (IV)

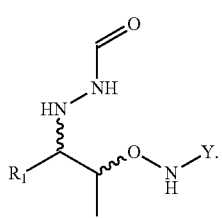

(IV)

According to this alternative conceivable process, it may not be necessary to carry out step (4) of the present invention.

While there are no specific restrictions as far as the nucleophilic compound comprising a nucleophilic residue $R_1$ is concerned with the proviso that reaction of this nucleophilic compound with the compound of formula (III) or with the compound of formula (II) allows for obtaining the compound of formula (IV), this nucleophilic compound is preferably a Grignard compound $R_1MgX$ wherein X is preferably selected from the group consisting of Cl, Br, and I. Preferably, residue $R_1$ is a straight or branched alkyl residue which preferably has from 1 to 6 carbon atoms, namely 1, 2, 3, 4, 5, or 6 carbon atoms, more preferably from 1 to 4 carbon atoms, namely 1, 2, 3, or 4 carbon atoms, more preferably 1 or 2 carbon atoms, in particular 2 carbon atoms.

Therefore, according to an especially preferred embodiment of the present invention, the nucleophilic compound comprising a nucleophilic residue $R_1$ is a Grignard compound $CH_3CH_2MgX$ wherein X is selected from the group consisting of Cl, Br, and I. In particular, the nucleophilic compound comprising a nucleophilic residue $R_1$ is $CH_3CH_2MgCl$.

The solvent or the solvents which is/are used for carrying out the reaction of step (5) of the present invention can be chosen to meet the requirements of the specific nature of the compound of formula (III) or of the compound of formula (II), and the specific nature of the nucleophilic compound. Preferably, the solvent used in reaction of step (5) of the present invention is toluene or at least one ether, wherein the ether is preferably selected from the group consisting of tetrahydrofurane (THF), MTBE, and a mixture of THF and MTBE.

The temperature at which the reaction according to step (5) is carried out will principally depend on the specific nature of the compound of formula (III) or of the compound of formula (II), the specific nature of the nucleophilic compound, and/or the solvent used. Preferred temperatures according to the present invention are in the range of from −80 to 0° C., preferably from −75 to −10° C., more preferably from −70 to −25° C.

An advantage of the process of the present invention is to be seen in the fact that steps (4), and (5) can be carried out in a single reaction vessel. No complicated transfers of reaction mixtures are necessary, allowing in particular for a simplified large-scale production.

Further, according to the present invention, a novel compound of formula (II) and also a novel compound of formula (III) is provided which surprisingly turned out to be more reactive towards Grignard reagents. Thus, in turn, the Grignard reaction described above can be carried out under mild conditions with essentially quantitative diastereoselectivity.

From the reaction mixture obtained from this step (5), the compound of formula (IV) may be separated, preferably after quenching the reaction with an appropriate reagent such as water or an alcohol. Preferably an alcohol is used for quenching, more preferably methanol is used. While there are no specific restrictions as to how such separation is carried out, solvent extraction is a preferred method according to the present invention. Prior to such extraction, a suitable solvent exchange may be carried out. According to the present invention, preferred extracting agents are selected from the group consisting of water preferably containing at least one suitable salt, organic ethers, organic esters, and a mixture of two or more thereof, wherein said salt is preferably selected from the group consisting of sodium chloride, sodium hydrogencarbonate, and ammonium chloride. More preferably, the extracting agent is water containing at least one suitable salt, preferably containing one suitable salt, more preferably containing ammonium chloride or sodium chloride. As far as the amount of salt contained in the water is concerned, typical embodiments are aqueous solutions containing 10 to 30 wt.-% of salt.

From the reaction mixture obtained, it is conceivable to suitably crystallize the compound of formula (IV) obtained from step (5). No specific restrictions exist as far as such crystallization is concerned with the proviso that at least a portion of the compound of formula (IV) crystallizes.

Therefore, the present invention also relates to the compound of formula (IV) as such

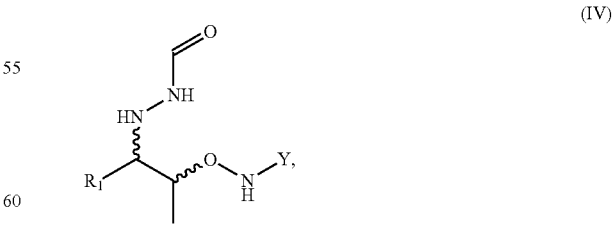

(IV)

which, according to a conceivable embodiment, may be at least partially crystalline, wherein Y is an optionally substituted aryl moiety, preferably an optionally substituted phenyl moiety, more preferably unsubstituted phenyl, wherein $R_1$ is preferably an alkyl residue preferably having from 1 to 6 carbon atoms, more preferably from 1 to 4 carbon atoms, more preferably 1 or 2 carbon atoms, most preferably 2 carbon atoms, $R_1$ in particular being ethyl, wherein preferably at least 95%, more preferably at least 97%, more preferably at least 99% of the molecules of said chiral compound are present as isomer of formula (IVa)

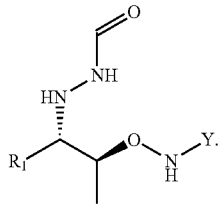

(IVa)

In particular, the present invention relates to the compound of formula (IV) with Y=phenyl and $R_1$=ethyl, which, according to a conceivable embodiment, may be at least partially crystalline, wherein at least 99% of the molecules of said optionally crystalline compound are present as isomer of formula (IVb)

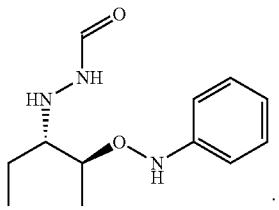

(IVb)

As mentioned above, according to step (5) of the present invention, the compound of formula (IV) is obtained, optionally after solvent extraction, contained in the solvent or solvent mixture used for the reaction of the compound of formula (III) with the nucleophilic compound. According to this embodiment, the compound of formula (IV) is not crystallized. According to an especially preferred embodiment of the present invention, this reaction mixture is subjected without further purification to a further step (6) which is described in detail hereinunder. As already indicated in the context of the reaction mixture obtained from step (4) and subjected to step (5), it is noted that also here, no further elaborate and tedious purification such as purification by chromatography is necessary, rendering the inventive process extremely straight-forward and extremely advantageous for large-scale productions.

Step (6)

According to a preferred embodiment of the present invention, the process of the present invention further comprises (6) reducing the compound of formula (IV), preferably by hydrogenation, to obtain a compound of formula (V)

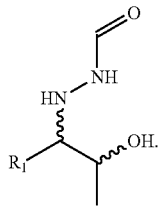

(V)

As far as reduction of the compound of formula (V) is concerned, hydrogenation is the preferred method. While being dependent on the specific chemical nature of compound (V) and the solvent used, hydrogenation according to the present invention is preferably carried out at a temperature in the range of from 15 to 35° C., preferably from 20 to 30° C. Typical temperature may be in the range of from 20 to 25° C. The hydrogen pressure under which the compound of formula (IV) is reduced is preferably in the range of from 0.5 to 50 bar, preferably from 1 to 20 bar, more preferably from 1 to 10 bar. Typical hydrogen pressures are, for example, in the range of from 1 to 5 bar or from 1 to 2 bar.

Typically, a suitable hydrogenation catalyst will be employed. While generally, homogeneous catalysts may be conceivable, heterogeneous catalysts are preferred. As heterogeneous catalysts, elements of the $8^{th}$, $9^{th}$; $10^{th}$, $11^{th}$, and $12^{th}$ subgroup of the PSE are conceivable. As examples, Pt, Rh, Ru, Co, Fe, Cu (such as in the form of copper chromite), Zn (such as in the form of zink chromite), Pd or Ni may be mentioned. According to the present invention, Pd is especially preferred. These elements may be suitably supported. For example, such supports may be mentioned which allow for a better distribution of the elements and a larger surface area. In particular as far as Pd is concerned, carbon is a preferred support. Thus, palladium on carbon, referred to herein as Pd/C, is an especially preferred catalyst according to the present invention.

Therefore, the present invention also relates to above-described process, wherein in (6), the hydrogenation is carried out at a temperature in the range of from 15 to 35° C., preferably from 20 to 30° C., at a hydrogen pressure in the range of from 0.5 to 50 bar, preferably from 1 to 20 bar, more preferably from 1 to 10 bar, in the presence of a precious metal containing catalyst, preferably a palladium containing catalyst, most preferably a Pd/C catalyst.

As far as the solvent in which reduction, preferably hydrogenation is carried out, is concerned, no specific restrictions exist with the proviso that at least a portion of the compound of formula (IV) is reduced. Preferably in the process of the present invention, a solvent mixture is employed which comprises at least one alcohol, preferably at least one alcohol having from 1 to 4 carbon atoms, namely 1, 2, 3, or 4 carbon atoms. More preferably, the solvent mixture comprises at least one alcohol having from 1 to 3 carbon atoms, namely 1, 2, or 3 carbon atoms. More preferably, the solvent mixture comprises at least one alcohol selected from the group consisting of methanol, ethanol, and isopropanol. The most preferred alcohol is methanol.

Apart from the at least one alcohol, most preferably methanol, the solvent mixture may further comprise at least one further solvent which is not an alcohol, preferably a further solvent which is selected from the group consisting of THF, toluene, MTBE, and a mixture of two or more thereof.

Thus, preferred solvent mixtures of the present invention employed for the reduction, preferably the hydrogenation according to step (6) of the present invention, comprise, more preferably essentially consist of at least one alcohol having from 1 to 4 carbon atoms, preferably at least one alcohol selected from the group consisting of methanol, ethanol, and isopropanol, and at least one solvent selected from the group consisting of THF, toluene, MTBE, and a mixture of two or more thereof. Especially preferred solvent mixtures of the present invention employed for the reduction, preferably the hydrogenation according to step (6) of the present invention, comprise, more preferably essentially consist of methanol and at least one solvent selected from the group consisting of THF, toluene, and MTBE, in particular MTBE.

From the reaction mixture obtained from above-described reduction, the reduction catalyst is preferably separated by at least one suitable method such as filtration. The thus separated catalyst may then be washed at least once, preferably with the same solvent or solvent mixture used for the reduction reaction, more preferably with the alcohol used in step (6).

Generally, according to a conceivable embodiment of the present invention, the compound of formula (V) obtained from step (6), most preferably after separation of the catalyst, may be used for an optional further reaction, as contained in the solvent or solvent mixture used for the reduction reaction and optionally the washing of the catalyst.

Surprisingly, it was found that the reductive cleaving according to step (6) of the present invention leads to the compound of formula (V) as crystalline compound. Therefore, according to a preferred embodiment of the present invention, the compound of formula (V) is crystallized. Therefore, the present invention relates to above-described process which further comprises crystallizing the compound of formula (V). In this context, it is noted that it is believed that according to the teaching of the prior art, in particular the teaching of WO 96/33163 wherein the non-crystalline benzyl-protected compound of formula (V) with $R_1$=ethyl is disclosed, the compound of formula (V) is not accessible as crystalline compound. Thus, the present invention should provide, for the first time, a process which allows for the preparation of the compound of formula (V) in crystalline form, having, according to an especially preferred embodiment of the present invention, a stereochemical purity of at least 99% with regard to the isomer of formula (Va) wherein said stereochemical purity is determined as described in Example 3 of the present invention. Further, the novel process involving the novel compounds described above, leads to a very good overall yield of the preferably crystalline compound of formula (V) which is about 30 to 40%, based on the starting material nitrosobenzene.

Therefore, the present invention also relates to a preferably, in particular a crystalline chiral compound according to formula (V)

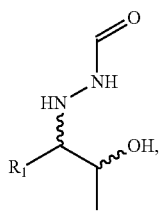

(V)

wherein $R_1$ is preferably an alkyl residue preferably having from 1 to 6 carbon atoms, more preferably from 1 to 4 carbon atoms, more preferably 1 or 2 carbon atoms, most preferably 2 carbon atoms, $R_1$ in particular being ethyl, wherein preferably at least 95%, preferably at least 97%, more preferably at least 99% of the molecules of said crystalline compound are present as isomer of formula (Va)

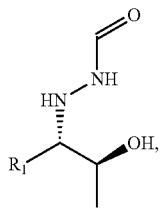

(Va)

in particular as isomer of formula (Vb)

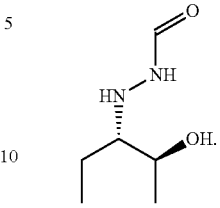

(Vb)

In particular, the present invention relates to the crystalline compound of formula (V) with $R_1$=ethyl,

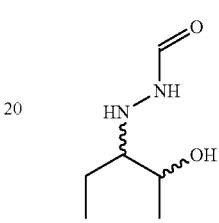

wherein preferably at least 95%, preferably at least 97%, more preferably at least 99% of the molecules of said crystalline compound are present as isomer of formula (Vb), which has an X-ray diffraction pattern comprising at least the following reflections:

| Diffraction angle 2 theta/° [Cu K(alpha 1)] | Relative Intensity (%) |
|---|---|
| 9.0 | 100 |
| 13.9 | 21 |
| 17.4 | 22 |
| 18.1 | 8 |
| 20.0 | 31 |
| 20.7 | 40 |
| 23.4 | 19 |
| 24.6 | 9 |
| 27.5 | 23 |
| 29.2 | 15 | wherein 100% relates to the intensity of the maximum peak in the X-ray diffraction pattern.

According to a preferred embodiment of the present invention, crystallization of the compound of formula (V) is carried out using a mixture of cyclohexane (CHX) and MTBE. The crystallization temperature is preferably in the range of from −10 to +10° C., more preferably from −5 to +5° C. Suitably seeding the reaction mixture obtained from (6) may further be carried out in order to improve the crystallization conditions.

After separation of the crystals, for example by suitable filtration, the crystals may be washed with a suitable washing agent, preferably a mixture of MTBE and CHX.

According to an optional embodiment of the present invention, the thus obtained crystalline compound of formula (V) may be re-crystallized at least once. Among other conceivable re-crystallization embodiments, re-crystallizing the compound of formula (V) may be preferably carried out in isopropyl acetate or in MIBK (methylisobutylketone) or in a mixture of isopropyl acetate and MIBK. Optionally, such re-crystallization may be carried out in the additional presence of at least one agent suitable for binding certain impurities still contained in the respective mixture. Among others, charcoal may be mentioned as suitable additional agent. Therefore, the present invention relates to above-described process, wherein after crystallization of the compound of formula (V), this compound is re-crystallized at least once in isopropyl acetate or in MIBK or in a mixture of isopropyl acetate and MIBK, optionally in the presence of charcoal.

The thus obtained crystals, either after crystallization and/or after re-crystallization, may be suitably dried. Preferably, the drying temperatures are in the range of from 10 to 40° C., more preferably from 15 to 35° C., more preferably from 20 to 30° C. at a pressure of less than 1 bar, preferably less than 500 mbar, more preferably less than 100 mbar.

As already indicated above, according to a preferred embodiment, the compound of formula (V), in particular of formula (V) with $R_1$=ethyl, is obtained, preferably as crystalline compound, with an enantiomeric purity of at least 99% with regard to the isomer of formula (Va), without the need to employ tedious purification methods such as purification by chromatography. Therefore, the present invention also relates to above-described process, wherein the compound of (V) is not subjected to purification by chromatography. Clearly, the process according to the present invention is thus highly superior to the prior art processes, in particular as far as medium-scale or large-scale production of the compound of formula (V) is concerned. Consequently, the process according to the present invention provides tremendous advantages especially for such processes according to which the compound of formula (V) is used as starting material for the production of widely used compounds such as, for example, antifungal agents.

Thus, the present invention in particular relates to the use of above-described process for the production of a starting material for the production of an antifungal agent, in particular posaconazole.

According to a first embodiment of the present invention, the preferably crystalline compound of formula (V), in particular the compound of formula (V) with $R_1$=ethyl, can be used as such for at least one further suitable reaction, such as starting material for the production of an antifungal agent, preferably posaconazole. For the sake of completeness, it is noted that the preferably crystalline compound can also be used for any conceivable reaction, and the use is not restricted to the use as starting material for the production of an antifungal agent.

According to a second embodiment of the present invention, the compound of formula (V), in particular the compound of formula (V) with $R_1$=ethyl, prior to being used as starting material for at least one further suitable reaction, such as starting material for the production of an antifungal agent, preferably posaconazole, may be optionally subjected to at least one reaction wherein the OH group is at least partially suitably protected. Generally, no particular restrictions exist with the proviso that the OH group is suitably protected. Generally conceivable groups are described, for example, in Greene et al., "Protective Groups in Organic Synthesis", 2nd ed., John Wiley & Sons, New York 1991 10-142.

Step (7)

According to an embodiment of the present invention, the OH group of the compound of formula (V) is suitably silylated. Preferably, silylation is carried out in order to provide a compound of formula (VI)

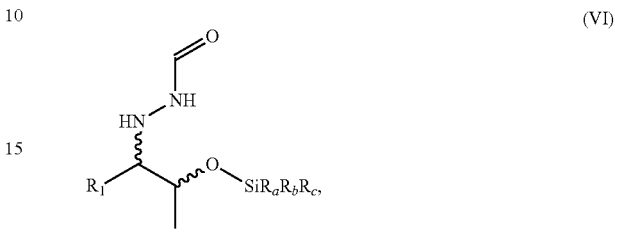

(VI)

wherein the residues $R_a$, $R_b$ and $R_c$ may be the same or different and are preferably alkyl or aryl residues. Therefore, the present invention relates to above-described process which further comprises (7) reacting the compound of formula (V) in a solvent with a silylating agent comprising the residue —$SiR_aR_bR_c$ to obtain a compound of formula (VI)

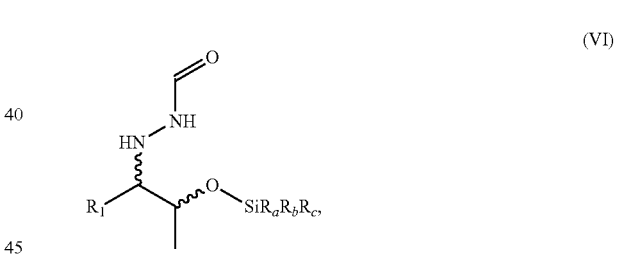

(VI)

wherein the residues $R_a$, $R_b$ and $R_c$ may be the same or different and are preferably alkyl or aryl residues.

The term "aryl residue" as used in this context of the present invention relates to a carbocyclic aromatic group, such as phenyl or naphthyl or the like. The term "alkyl residue" as used in the context of the present invention relates to straight or branched alkyl moieties which preferably have 1, 2, 3, 4, 5, or 6 carbon atoms.

According to a conceivable embodiment of the present invention, the compound of formula (VI) may be suitably crystallized.

Therefore, the present invention also relates to an optionally crystalline chiral compound according to formula (VI) as such,

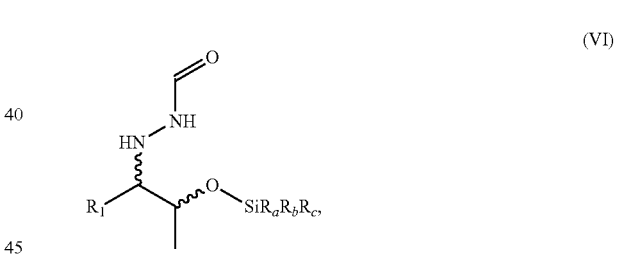

(VI)

wherein $R_1$ is preferably an alkyl residue preferably having from 1 to 6 carbon atoms, more preferably from 1 to 4 carbon atoms, more preferably 1 or 2 carbon atoms, most preferably 2 carbon atoms, $R_1$ in particular being ethyl, wherein the residues $R_a$, $R_b$ and $R_c$ may be the to same or different and are preferably alkyl or aryl residues, wherein preferably at least 95%, more preferably at least 97%, more preferably at least 99% of the molecules of said optionally crystalline compound are present as isomer of formula (VIa)

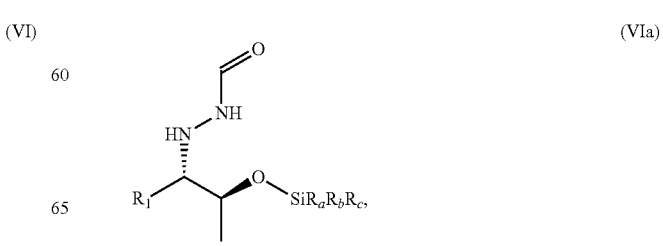

(VIa)

in particular as isomer of formula (VIb))

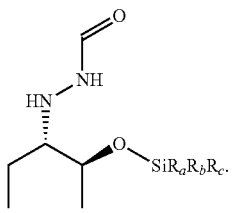
(VIb)

Purity of compound of formula (VI) may be determined according to known methods of the art.

Generally, the present invention also relates to a chiral compound, obtainable or obtained by a process involving any of the steps as described above. In particular, the present invention relates to a chiral compound, obtainable or obtained by a process comprising the steps (1), (2) and (3), or comprising the steps (1), (2), (3) and (4), or comprising the steps (1), (2), (3), (4) and (5), or comprising the steps (1), (2), (3), and (5) without step (4), or comprising the steps (1), (2), (3), (4), (5) and (6), or comprising the steps (1), (2), (3), (5) and (6) without step (4), or comprising the steps (1), (2), (3), (4), (5), (6) and (7), or comprising the steps (1), (2), (3), (5), (6) and (7) without step (4).

Further, according to a conceivable embodiment, the present invention also relates to at least one suitable salt of the compound of formula (II) and/or to at least one suitable salt of the compound of formula (III) and/or to at least one suitable salt of the compound of formula (IV) and/or to at least one suitable salt of the compound of formula (V) and/or to at least one suitable salt of the compound of formula (VI).

Use

As already indicated above, the preferably crystalline compound of formula (V) and/or the optionally crystalline compound of formula (VI), both optionally obtained or obtainable by a process according to the present invention, preferably the crystalline compound of formula (V) with $R_1$=ethyl

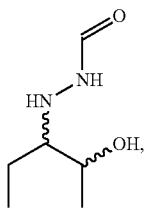

wherein preferably at least 95%, more preferably at least 97%, and especially preferably at least 99% of the molecules of said crystalline compound are present as isomer of formula (Vb)

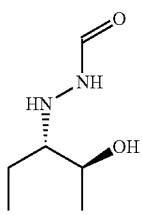
(Vb)

is used as starting material for a further reaction, in particular as starting material for the preparation of an antifungal agent.

Thus, the present invention also relates to a method for the preparation of an antifungal agent, wherein the preferably crystalline compound of formula (V), in particular the preferably crystalline compound of formula (V) with $R_1$=ethyl, and/or the optionally crystalline compound of formula (VI), in particular the optionally crystalline compound of formula (VI) with $R_1$=ethyl, both optionally obtained or obtainable by a process according to the present invention, preferably the crystalline compound of formula (V) with $R_1$=ethyl

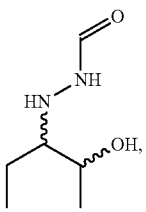

wherein preferably at least 95%, more preferably at least 97%, and especially preferably at least 99% of the molecules of said crystalline compound are present as isomer of formula (Vb)

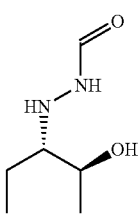
(Vb)

is/are used as starting material for a further reaction, in particular as starting material for the preparation of an antifungal agent.

According to a preferred use or method of the present invention, the preferably crystalline compound of formula (V) with $R_1$=ethyl and/or the optionally crystalline compound of formula (VI) with $R_1$=ethyl, optionally obtained or obtainable by a process according to the present invention, preferably the crystalline compound of formula (V) with $R_1$=ethyl, is reacted with aniline or a derivative thereof and phosgene or a derivative thereof or an isocyanate, preferably a phosgene derivative.

While there are no specific restrictions as to the chemical nature of the derivative of aniline with the proviso that an antifungal agent is finally obtained, the aniline derivative is preferably a compound of formula:

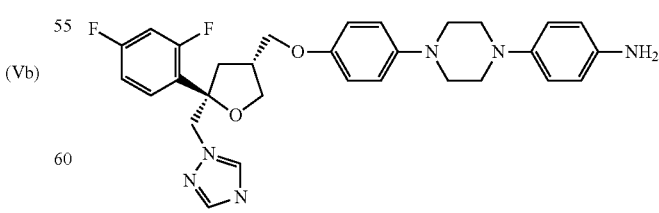

While there are no specific restrictions as to the chemical nature of the derivative of phosgene with the proviso that an antifungal agent is finally obtained, the phosgene derivative is preferably a compound of formula:

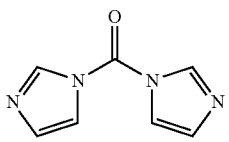

According to an especially preferred use or method of the present invention, the finally obtained antifungal agent is posaconazole of formula:

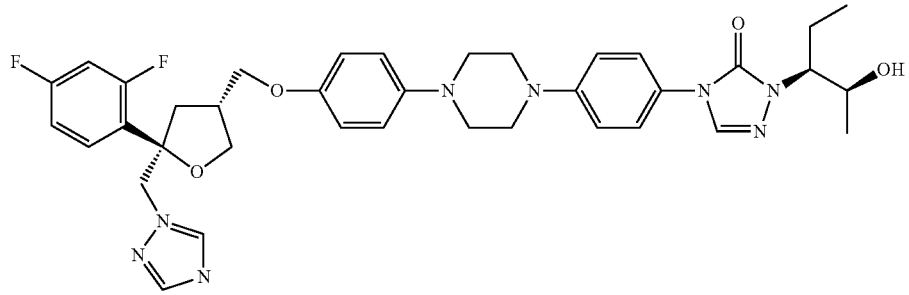

The present invention is further illustrated by the following examples.

EXAMPLES

Example 1

Synthesis of the Compound of Formula (II) with Y=phenyl a) 1.70 kg of nitrosobenzene (MW: 107.11; 15.9 mol; 1.0 eq.) were dissolved in 6.16 L of DCM by stirring at 20-25° C. under $N_2$ atmosphere.
b) In a separate vessel, 2.76 kg propionaldehyde (MW: 58.08; density: 0.798 g/mL; 47.5 mol; 3.0 eq.) and 5.28 L of DCM were cooled to −6 to −4° C. under $N_2$ atmosphere. To the resulting mixture, 0.057 kg of glacial acetic acid (MW: 60.05; density: 1.049 g/mL; 0.95 mol; 0.06 eq.) and 0.55 kg of D-proline (MW: 115.13; 4.75 mol; 0.3 eq.) were added, and a fine suspension was obtained.
c) To this suspension of b), 0.4 L of the nitrosobenzene solution obtained in a) were added. Onset of the reaction was indicated by discoloration of the suspension and a temperature rise up to +3° C. within 1 min. Then, the remaining nitrosobenzene solution (about 7 L) of the nitrosobenzene solution obtained in a) were added at a rate to keep the reaction temperature between −5 and −3° C. The mixture gradually turned darker and resulted in a clear solution when addition was complete. Stirring was then continued for 10 min, and complete conversion was determined using HPLC. The compound of formula (I) with Y=phenyl was obtained as intermediate with an enantiomeric purity expressed as enantiomeric excess (ee)>98%, i.e. more than 99% of the molecules of the chiral compound of formula (I) with Y=phenyl were present as isomer of formula (Ia) with Y=phenyl. Enantiomeric purity was determined analogously to the method described in Brown et al., *J. Chem. Soc.* 2003, 125 (36), 10808-10809 and using Chiralcel OD-H and n-heptane/isopropanol/diethylamine as eluent.
d) Subsequently, 8.8 L of DCM, 3.0 kg of a molecular sieve having pores with a diameter of 0.4 nm (nanometre; 4 Angstrom; commercially available from Aldrich), and 3.14 kg of formyl hydrazine (MW: 60.06; 52 mol; 3.3 eq.) were added at 0-5° C., leading to an increase in temperature. Stirring was continued at 0-5° C. under $N_2$ atmosphere. After 3 hours, complete conversion was determined using HPLC.
e) The obtained solids were filtered and washed with 4.4 L of DCM. The solution was concentrated to ¼ of its original volume at a bath temperature of <10° C. Then, 28 L of MTBE were added, and the resulting solution was reduced to ¼ of its original volume by distillation at a bath temperature of <10° C. The resulting organic layer was then diluted with 7 L of MTBE and extracted five times with 28 L of a 20% aqueous sodium chloride solution. Then, 8.8 L of DCM were added for azeotropic removal of water. The resulting solution was concentrated to give 12 kg of a solution of the compound of formula (II) with Y=phenyl in MTBE which contained 2.86 kg of said compound (MW 207.23; 80% yield).
f) This solution containing the compound of formula (II) with Y=phenyl was used in the next step (Example 2) without further purification.

Example 2

Synthesis of the Compounds of Formula (III) and (IV) with Y=phenyl, and $R_{aa}$, $R_{bb}$ and $R_{cc}$=methyl and $R_1$=ethyl a) 0.887 kg of the compound of formula (II) as obtained according to Example 1 (MW: 207.23; 4.28 mol; 1.0 eq.), employed as a solution in MTBE (total weight 290 g) which contained about 2 wt.-% of $H_2O$, were dried with 1.54 of a molecular sieve having pores with a pore diameter of 0 4 nm (4 Angstrom; commercially available from Aldrich) at 20-25° C. for 30 min. Thus, the water content was reduced to a value of less than 0.1 wt.-%. Then, the molecular sieve was removed by filtration and washed with 1.7 L of MTBE. The resulting solution was diluted with 16 L of MTBE. The water content of this solution was about 0.05% (0.5 mol; 0.12 eq.).
b) Then, 2.8 L of BSA (bistrimethylsilylacetamide) (MW: 203.43; density: 0.832 g/mL; 11.5 mol; 2.7 eq.) were added to the filtrate. The resulting solution was stirred at 20-25° C. After 1 hour, silylation was complete, as detected by $^1$H-NMR. The compound of formula (III) with Y=phenyl and $R_{aa}$, $R_{bb}$ and $R_{cc}$=methyl was obtained as intermediate.
c) Then, the solution was cooled to −70 to −60° C., and 8.65 L of a solution of ethyl magnesium chloride in THF (2 mol/l; MW: 88.82; density: 0.978 g/ml; 17.3 mol; 4.0 eq.)

were added at a rate to keep the reaction temperature between −70 and −60° C. This mixture was stirred for 1 hour at −60° C. Subsequently, the temperature was raised to −25° C., and stirring was continued. After 3 hours, complete conversion was detected by HPLC. The reaction was then quenched by dropwise addition of 5.5 kg of MeOH at a temperature of −25° C. During quenching, the mixture was allowed to warm up to 0-15° C.

d) The resulting organic layer was then extracted at 20-25° C. twice with 30 L of a 10% aqueous ammonium chloride solution and once with 30 L of a 20% aqueous sodium chloride solution. The organic layer (20 kg) contained approximately 0.89 kg of the compound of formula (IV) with Y=phenyl and $R_1$=ethyl (MW: 237.30; 80% yield) and was used for the next step (Example 3) without further purification.

Example 3

Synthesis of the Compounds of Formula (V) with $R_1$=ethyl a) 0.89 kg of the compound of formula (IV) (MW: 237.30; 3.76 mol; 1.0 eq.), obtained according to Example 2 and used as a solution in MTBE (total weight 20 kg) was diluted with 1 L of MeOH at 20-25° C.

b) Then, 0.9 kg of palladium on carbon (Pd/C; 5% Pd; 50% water) were added, and the resulting solution was stirred vigorously at 20-25° C. Reduction reaction was carried out with 1 atm of $H_2$. The vessel was evacuated and vented with 1 atm $H_2$ three times. After 1.5 hours of stirring under $H_2$ atmosphere, complete conversion was detected by HPLC. Then, the suspension was filtrated and the catalyst washed with 1.8 L of MTBE/MeOH (1/1 v/v). The combined filtrates were concentrated to a yellow oil to yield the crude compound of formula (V) with $R_1$=ethyl, containing about 40% (about 0.55 kg) of the compound of formula (V) with $R_1$=ethyl.

c) This oil was diluted with 13.9 L of MTBE at 20-25° C., and the resulting solution was seeded. After 1 hour of stirring at 20-25° C., a fine suspension was obtained. Then, 17 L of CHX (cyclohexane) were added, the mixture was cooled to 0° C. and stirred at 0° C. for 3 hours, resulting in a thick suspension of the compound of formula (V) with $R_1$=ethyl. The thus obtained crystals were collected and washed with 2.2 L of a cold (0° C.) mixture of MTBE and CHX (1/1 v/v) to give 0.44 kg of the compound of formula (V) with $R_1$=ethyl after drying (MW 146.19; 80% yield; 64% yield with respect to the compound of formula (II)). More than 99% of the molecules of the chiral compound of formula (V) with $R_1$=ethyl were obtained as isomer according to formula (Vb).

10.4 g of this yellow colored material were added to 50 mL of isopropyl acetate, and the resulting mixture was heated to a temperature of 85 to 89° C. until a solution was obtained. 0.5 g of activated carbon were added to the yellow solution, and after stirring for several minutes, the hot mixture was filtered and allowed to cool to about 5° C. under stirring. After stirring for 2 to 3 hours, the precipitated product was filtered, washed with 5 mL of isopropyl acetate and dried at room temperature under vacuum over night to give 8.54 g of the product as a off-white solid (melting point 78 to 80° C.), i.e. the compound of formula (V) with $R_1$=ethyl, wherein more than 99% of the molecules of said compound were obtained as isomer according to formula (Vb).

Preparation of seeds used in this step c):

100 g of the crude oil obtained in step b) where purified by column chromatography using 800 g silica gel 60 (0.063-0.200 mm, Merck) as stationary phase and DCM/methanol=20/1 as mobile phase. The fractions containing the desired product in pure form, as determined by TLC (Merck, silica gel 60 $F_{254}$, mobile phase CHX/ethyl acetate=1/1), where collected. After evaporation of the solvents the obtained solid was recrystallized from diethyl ether. The resulting crystals where collected and used as seeds after drying (20° C., <100 mbar).

d) The IR spectrum and the X-ray diffractogram are shown in FIGS. 1 and 2.

Experimental data were obtained as follows:

The enantiomeric purity of the compound of formula (V) with $R_1$ mm ethyl as obtained in c) was measured by HPLC as follows:

Chromatography
HPLC apparatus: Agilent 1200
Column: Waters XBridge C18, 2.5 μm, 50×4.6 mm (order no. 186003090)
System: gradient
Eluent A: buffer solution pH 7.0
Eluent B: buffer solution pH 7.0/acetonitrile=2/8 (v/v)
Flow rate: 1.8 mL/min
Oven temperature: 40° C.
Injection volume: 10 μL (microliter)
Stop time: 20 min
Detection: λ (lambda)=260 nm
Gradient:

| | t (min) | | | | | |
|---|---|---|---|---|---|---|
| | 0 | 8 | 12 | 14 | 15 | 20 |
| % B | 10 | 20 | 100 | 100 | 10 | 10 |

Buffer solution pH 7.0 prepared according to the following recipe: dissolve 7.0 mL of triethylamine in 900 mL of water, adjust the pH to 7.0 with $H_3PO_4$ and dilute to 1000 mL with water.

Reagent solution prepared according to the following recipe: dissolve 80 to 90 mg of (S)-(−)-α-methylbenzyl isocyanate in acetonitrile and dilute to 1.0 mL with acetonitrile.

Sample preparation:
a) Test stock solution prepared according to the following recipe:
Dissolve 38 to 42 mg of the substance to be tested, weighed accurately to 0.01 mg, in 1.0 mL of acetonitrile.
b) Test solution prepared according to the following recipe:
In an HPLC vial, mix 100 μL (microliter) of test stock solution and 100 μL (microliter) of reagent solution. Keep at room temperature (20 to 25° C.) for 30 min, add 800 μL (microliter) of buffer solution pH 7.0 and shake well. Then cool the solution on an ice bath (0° C.) for additional 30 min (precipitation of reagent) and filtrate a sample through 0.2 μm (micrometer) directly into another HPLC vial.

Infrared spectra (IR) data were collected on a MKII Golden Gate™ Single Reflection Diamond ATR (attenuated total reflection) cell with a Bruker Tensor 27 FTIR spectrometer with 4 $cm^{-1}$ resolution at ambient conditions. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

X-ray data (powder diffraction pattern XRPD, X-ray diffractogram) were collected on a Unisantis XMD 300 X-ray powder diffractometer with a position sensitive detector in parallel beam optics using the following acquisition conditions: tube anode: Cu, 40 kV, 0.8 mA; 3-43° theta/2theta; simultaneous detection of regions of 10° per step with detector resolution 1024, counting time 300 seconds per step. Samples were measured at room temperature in a standard sample holder on a rotating sample spinner. A typical precision of the 2-theta values is in the range of ± about 0.2° 2-Theta. Thus a diffraction peak that appears at 5.0° 2-Theta can appear between 4.8 and 5.2° 2-Theta on most X-ray diffractometers under standard conditions.

HPLC for determination of completion of conversion as mentioned in Example 1, c) and d), Example 2), c) and Example 3, b) was performed as follows:

Column: Zorbax Eclipse XDB-C18, 150*4.6 mm, 5 μm (micrometer).
System: gradient
Buffer: 2.10 g KH$_2$PO$_4$+4.28 g K$_2$HPO$_4$/2.0 L H$_2$O, adjust with 85% H$_3$PO$_4$ to pH 6.5
Mobile phase A: 20 mM phosphate buffer pH 6.5/acetonitrile, 85/15, v/v
Mobile phase B: 20 mM phosphate buffer pH 6.5/acetonitrile, 50/50, v/v
Solvent: H$_2$O/acetonitrile=50/50 v/v
Flow rate: 1.5 mL/min
Oven temperature: 60° C.
Injection volume: 5-20 μL (microliter)
Stop time: 30 min
Detection: λ (lambda)=210 nm (Agilent 1200 detector)
Autosampler: 5° C.
Gradient:

| t [min] | | | | |
|---|---|---|---|---|
| 0 | 20 | 25 | 26 | 30 |
| % B | 5 | 100 | 100 | 5 | stop |

Sample Preparation:

Sample solution for HPLC in Example 1), c) was prepared according to the following recipe: dissolve approx. 100 μL (microliter) of the reaction mixture in 0.2 mL of isopropanol, add approx. 50 mg of NaBH$_4$ and agitate for 10 min at 25° C. Extract with 0.2 mL of ethyl acetate and 0.5 mL of a 5% KH$_2$PO$_4$ buffer (pH 7.0). Dilute 50 L (microliter) of the resulting organic layer in a 10 mL volumetric flask and fill to the mark. with solvent. Sample weights are adapted according to instrument requirements.

Sample solution for HPLC for Example 1), d), Example 2), c) and Example 3), b) was prepared according to the following recipe: dissolve approx. 100 μL of the reaction mixture in 2 mL of acetonitrile in a 20 mL volumetric flask and fill to the mark with solvent. Sample weights are adapted according to instrument requirements.

List Of Cited Documents
WO 95/17407
WO 97/22579
Saksena et al., *Tetrahedron Lett.* 2004, 45 (44), 8249-8251
WO 96/33163
WO 97/33178
Brown et al., *J. Chem. Soc.* 2003, 125 (36), 10808-10809
Cordova et al., *Chem. Eur. J.* 2004, 10 (15), 3673-3684
Hayashi et al., *J. Org. Chem.* 2005, 69 (18), 5966-5973
Greene et al., "Protective Groups in Organic Synthesis", 2nd ed., John Wiley & Sons, New York 1991 10-142

The invention claimed is:

1. An optionally crystalline chiral compound of formula (II)

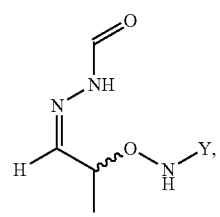

wherein Y is an optionally substituted aryl moiety, wherein at least 95% of the molecules of said optionally crystalline compound are present as isomer of formula (IIa)

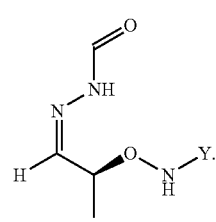

2. A chiral compound of formula (IV)

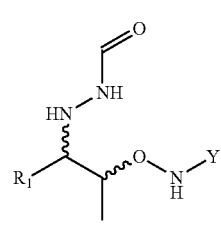

wherein Y is an optionally substituted aryl moiety, wherein R$_1$ is an alkyl residue having from 1 to 6 carbon atoms, wherein at least 95% of the molecules of said chiral compound are present as isomer of formula (IVa)

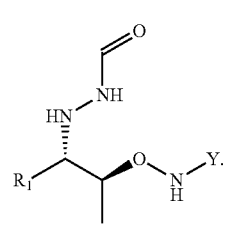

3. The optionally crystalline chiral compound of claim 1, wherein Y is an optionally substituted phenyl moiety.

4. The optionally crystalline chiral compound of claim 1, wherein Y is an unsubstituted phenyl.

5. The optionally crystalline chiral compound of claim 1, wherein at least 97% of the molecules of said optionally crystalline compound are present as isomer of formula (IIa).

6. The optionally crystalline chiral compound of claim 1, wherein at least 99% of the molecules of said optionally crystalline compound are present as isomer of formula (IIa).

7. The optionally crystalline chiral compound of claim 2, wherein Y is an optionally substituted phenyl moiety.

8. The optionally crystalline chiral compound of claim 2, wherein Y is an unsubstituted phenyl.

9. The optionally crystalline chiral compound of claim 2, wherein at least 97% of the molecules of said chiral compound are present as isomer of formula (IVa).

10. The optionally crystalline chiral compound of claim 2, wherein at least 99% of the molecules of said chiral compound are present as isomer of formula (IVa).

11. A process for the preparation of a chiral compound, comprising
(1) providing a chiral compound of formula (I)

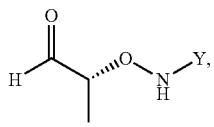
(I)

wherein Y is an optionally substituted aryl moiety;
(2) reacting the compound of formula (I) with $H_2N$—NH—CHO in a solvent to obtain a compound according to formula (II)

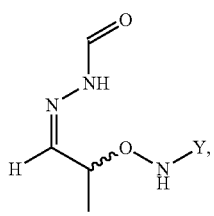
(II)

wherein at least 95% of the molecules of said optionally crystalline compound are present as isomer of formula (IIa)

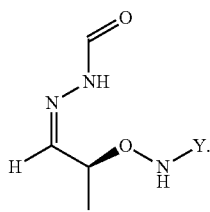
(IIa)

12. The process of claim 11, wherein in (1), the compound of formula (I) is provided by reacting propionaldehyde in a solvent with a compound of formula (i)

O═N—Y (i), in the presence of a catalyst system, said catalyst system optionally further comprising a promoter.

13. The process of claim 12, wherein the reaction of propionaldehyde with the compound of formula (i) is carried out at a temperature in the range of from −15 to +5° C. in dichloromethane (DCM) as solvent.

14. The process of claim 12, wherein the reaction of propionaldehyde with the compound of formula (i) is carried out in the presence of a catalytical amount of an acid.

15. The process of claim 11, wherein in (2), the compound of formula (I) is reacted with $H_2N$—NH—CHO in the presence of a molecular sieve.

16. The process of claim 11, wherein in (2), the compound of formula (I) is reacted with $H_2N$—NH—CHO at a temperature in the range of from −10 to +20° C. in dichloromethane (DCM) as solvent.

17. The process of claim 11, wherein after (1), the compound of formula (I) is not separated from the reaction mixture obtained from (1) prior to reaction with $H_2N$—NH—CHO in (2).

18. The process of claim 11, further comprising
(3) separating the compound of formula (II) from the reaction mixture obtained from (2) by solvent extraction, wherein prior to (3), a solvent exchange is carried out.

19. The process of claim 11, further comprising
(4) reacting the compound of formula (II) in a solvent with a silylating agent comprising the residue —$SiR_{aa}R_{bb}R_{cc}$ to obtain a compound of formula (III)

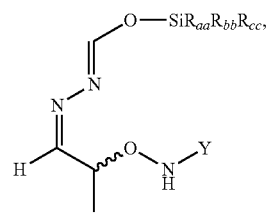
(III)

wherein the residues $R_{aa}$, $R_{bb}$ and $R_{cc}$ may be the same or different and are alkyl or aryl residues having from 1 to 6 carbon atoms.

20. The process of claim 19, wherein the silylating agent is hexamethyldisilazane, trimethylchlorosilane, bistrimethylsilylacetamide or a mixture of two or three of these compounds.

21. The process of claim 19, wherein the reaction in (4) is carried out at a temperature in the range of from 15 to 70° C.

22. The process of claim 11, further comprising
(5) reacting the compound of formula (II) or reacting the compound of formula (III) with a nucleophilic compound comprising a nucleophilic residue $R_1$ in a solvent to obtain a compound of formula (IV)

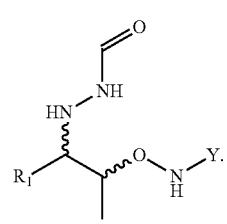
(IV)

23. The process of claim 22, wherein the nucleophilic compound is a Grignard compound $R_1MgX$ wherein X is selected from the group consisting of Cl, Br, and I, and wherein $R_1$ is an alkyl residue having from 1 to 6 carbon atoms.

24. The process of claim 22, wherein the nucleophilic compound is $CH_3CH_2MgCl$.

25. The process of claim 22, wherein in (5), the compound of formula (II) or the compound of formula (III) is reacted with the nucleophilic compound at a temperature in the range of from −80 to 0° C.

26. The process of claim 22, wherein for the reaction of the compound of formula (II) or of the compound of formula (III) with the nucleophilic compound in (5), toluene or at least one ether is used as solvent.

27. The process of claim 22, wherein after (4), the compound of formula (III) is not separated from the reaction mixture obtained from (4) prior to reaction with the nucleophilic compound in (5).

28. The process of claim 22, further comprising
(6) reducing the compound of formula (IV) by hydrogenation, to obtain a compound of formula (V)

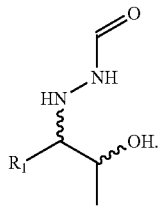

(V)

29. The process of claim 28, wherein in (6), the hydrogenation is carried out at a temperature in the range of from 15 to 35° C., at a hydrogen pressure in the range of from 0.5 to 50 bar, in the presence of a precious metal containing catalyst.

30. The process of claim 28, wherein for reducing the compound of formula (IV) in (6), a solvent mixture comprising at least one alcohol comprising 1 to 4 carbon atoms.

31. The process of claim 30, further comprising crystallizing the compound of formula (V).

32. The process of claim 31, wherein the compound of formula (V) is crystallized from a mixture of MTBE and cyclohexane (CHX).

33. The process of claim 28, wherein the compound of formula (V) is not subjected to purification by chromatography.

34. The process of claim 28, further comprising
(7) reacting the compound of formula (V) in a solvent with a silylating agent comprising the residue —$SiR_aR_bR_c$ to obtain a compound of formula (VI)

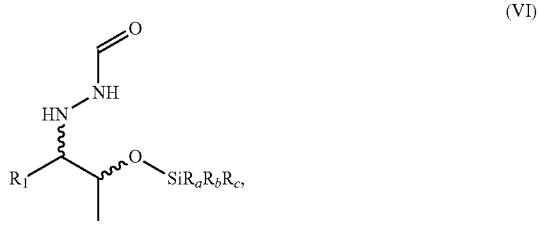

(VI)

wherein the residues $R_a$, $R_b$ and $R_c$ may be the same or different and are alkyl or aryl residues.

35. The process of claim 11, wherein at least 95%, of the molecules of the chiral compound of formula (I) provided in (1) are present as isomer of formula (Ia)

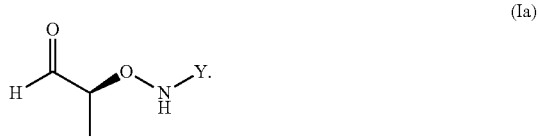

(Ia)

* * * * *